United States Patent [19]

Huth et al.

[11] Patent Number: 4,600,715

[45] Date of Patent: Jul. 15, 1986

[54] BENZODIAZEPINE ANTAGONISTIC β-CARBOLINE DERIVATIVES AND COMPOSITIONS THEREOF

[75] Inventors: Andreas Huth; Ralph Schmiechen; Dieter Seidelmann; Dieter Rahtz, all of Berlin, Fed. Rep. of Germany; Mogens Engelstoft, Vaerlose; Claus T. Braestrup, Roskilde, both of Denmark

[73] Assignee: Shering Aktiengesellschaft, Berlin, Fed. Rep. of Germany

[21] Appl. No.: 623,671

[22] Filed: Jun. 22, 1984

[30] Foreign Application Priority Data

Jun. 23, 1983 [DE] Fed. Rep. of Germany ....... 3322894

[51] Int. Cl.[4] .................. A61K 31/68; A61K 31/535; C07D 471/06; C07D 403/06
[52] U.S. Cl. ..................................... 514/222; 514/234; 514/236; 514/292; 544/60; 544/126; 544/361; 546/85; 546/87
[58] Field of Search .................. 544/60, 126, 361; 546/85, 87; 424/246, 248.53, 248.54, 250, 256; 514/292, 222, 233, 234, 236

[56] References Cited

U.S. PATENT DOCUMENTS 4,371,536 2/1983 Braestrup et al. ............... 424/256
4,435,403 3/1984 Braestrup et al. ............... 424/256

OTHER PUBLICATIONS

Neef et al., CA 99 (1983), p. 742.

Primary Examiner—Henry R. Jiles
Assistant Examiner—J. G. Mullins
Attorney, Agent, or Firm—Millen & White

[57] ABSTRACT

β-carboline derivatives of general Formula I

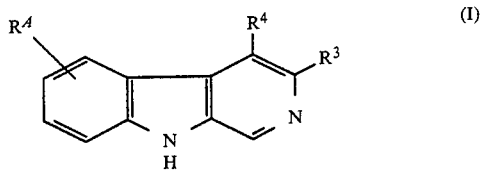

wherein $R^3$ is

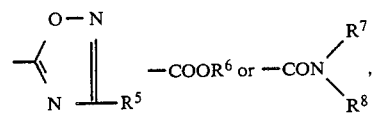

wherein $R^5$ is $C_{1-5}$ alkyl, $R^6$ is lower alkyl, aralkyl, or alkoxyalkyl of up to 7 carbon atoms, and $R^7$ and $R^8$ are hydrogen $C_{1-5}$ alkyl, or, collectively with the amido nitrogen atom, piperidino,
$R^4$ is hydrogen, $C_{1-3}$ alkyl, or $CH_2OR^9$ wherein $R^9$ is $C_{1-3}$ alkyl, atoms, and
$R^4$ is —$COOR^{10}$

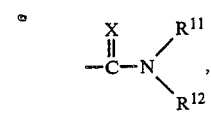

wherein $R^{10}$ is hydrogen, lower alkyl, alkoxyalkyl or alkenyl of up to 5 carbon atoms, or benzyl, or X is oxygen or sulfur, and $R^{11}$ and $R^{12}$ each are hydrogen, lower alkyl or alkenyl or, collectively with the amido nitrogen atom, represent a hetero ring, are prepared by conventional methods and exhibit, inter alia, an effect on the central nervous system and are suitable for use as psychopharmaceuticals.

44 Claims, No Drawings

BENZODIAZEPINE ANTAGONISTIC β-CARBOLINE DERIVATIVES AND COMPOSITIONS THEREOF

BACKGROUND OF THE INVENTION

This invention relates to novel substituted β-carbolines, and pharmaceutical compositions comprising them to a process for the preparation thereof, and to the use thereof as medicinal agents.

SUMMARY OF THE INVENTION

In a composition aspect, this invention relates to β-carbolines of general Formula I

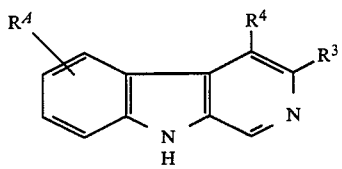

wherein
$R^3$ is an oxadiazolyl group of the formula

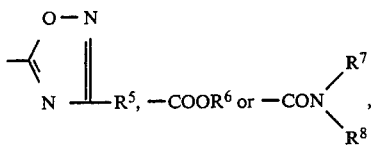

wherein $R^5$ is lower alkyl of up to 5 carbon atoms, $R^6$ is lower alkyl, aralkyl, or alkoxyalkyl of up to 7 carbon atoms, and $R^7$ and $R^8$, which are alike or different, each are hydrogen or lower alkyl of up to 5 carbon atoms or collectively form with the amido nitrogen atom a piperidino ring;
$R^4$ is hydrogen, lower alkyl of up to 3 carbon atoms or $CH_2OR^9$ wherein $R^9$ is lower alkyl of up to 3 carbon atoms; and
$R^A$ is in the 5- or 6-position and is $-COOR^{10}$ or

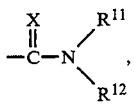

wherein $R^{10}$ is hydrogen or lower alkyl, alkoxyalkyl or alkenyl of up to 5 carbon atoms, or benzyl, wherein X is oxygen or sulfur and $R^{11}$ and $R^{12}$, which are alike or different, are hydrogen, lower alkyl or lower alkenyl or, collectively with the amido nitrogen atom, form a nitrogen-containing 5- or 6-membered hetero ring which can contain as a further hetero ring atom oxygen, sulfur, nitrogen, methyl-substituted nitrogen or phenyl-substituted nitrogen.

In a process aspect, this invention relates to a process for the production of β-carbolines of general Formula I wherein (a) in a conventional manner, a substituted β-carboline of general Formula II

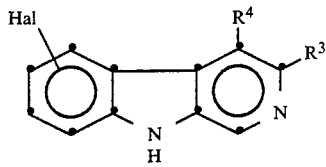

wherein
$R^3$ and $R^4$ have the values given above and
Hal is bromine or iodine,
is reacted in the presence of an organic base with carbon monoxide and an organic alcohol of the formula $R^6OH$, wherein $R^6$ is alkyl, aralkyl, or alkoxyalkyl; or (b) a substituted β-carboline derivative of Formula III

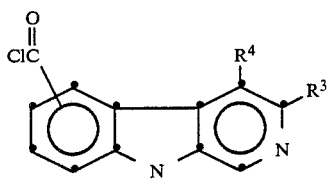

wherein $R^3$ and $R^4$ have the above values given, is reacted with a primary or secondary amine of the formula $HNR^{11}R^{12}$ wherein $R^{11}$ and $R^{12}$ have the values given above; or (c) a substituted β-carboline-3-carboxylic acid of general Formula IV

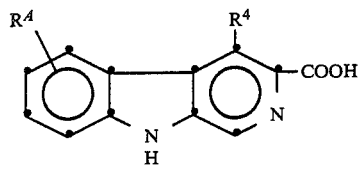

wherein $R^A$ and $R^4$ have the above-indicated meanings, is reacted with an amidoxime of the general formula $R^5-C(=NOH)NH_2$ wherein $R^5$ has the above values given, to the 5-oxadiazolyl derivative or, with piperidine in the presence of triethylamine and ethyl chloroformate, to the 3-carboxylic acid piperidide and, optionally, an aralkoxy group is reductively converted by hydrogenolysis partially to the free acid, and/or an ester of an aliphatic alcohol is completely hydrolyzed in an alkaline reaction and, if desired, the free acid is reesterified with an alcohol in the presence of cesium carbonate and optionally the carbonyl oxygen is replaced by sulfur.

In a further composition aspect, this invention relates to pharmaceutical compositions comprising a compound of general Formula I in admixture with a pharmaceutically acceptable carrier.

In a method of use aspect, this invention relates to the use of compounds of general Formula I as psychopharmaceuticals.

DETAILED DISCUSSION

Examples of groups of compounds of general Formula I are those wherein:

(a) $R^A$ is in the 6-position;

(b) $R^3$ is —COOR$^6$ and $R^4$ is —COOR$^{10}$ in which $R^6$ and $R^{10}$ have the values given therein, e.g., those of Group (a);

(c) $R^3$ is —COOR$^6$ and $R^4$ is —CONR$^{11}$R$^{12}$ in which $R^6$, $R^{11}$ and $R^{12}$ have the values given therein, e.g., those of Groups (a) and (b);

(d) $R^4$ is CH$_3$, e.g., those of Groups (a), (b) and (c);

(e) $R^4$ is H, e.g., those of Groups (a), (b) and (c); and (f) $R^4$ is CH$_3$OCH$_2$, e.g., those of Groups (a), (b) and (c).

The novel β-carbolines of general Formula I may be substituted in the 3-position by a 3-substituted-5-oxadiazolyl group and in the A-ring by an aminocarbonyl or with an alkoxycarbonyl group.

Examples of 3-substituents on the 5-oxadiazolyl group are methyl, ethyl, n-propyl, isopropyl, cyclopropyl, cyclopentyl, cyclohexyl, carbomethoxy, carbethoxy, carbopropoxy and carbobutoxy.

In Formulae I-IV alkyl can be straight-chain or branched-chain, e.g., methyl, ethyl, propyl, isopropyl, n-butyl, isobutyl and tert-butyl.

The 4-position substituent of the novel β-carbolines is hydrogen, lower alkyl, e.g., methyl or ethyl, or lower alkoxymethyl.

The $R^4$ substituent can be in the 5- or 6-position with the 6-position being preferred. The heterocyclic amino substituents can contain from 0-2 ring heteroatoms, e.g., N, S and/or O, in addition to the amido nitrogen atom.

The compounds of this invention exhibit valuable pharmacological activities, including anticonvulsant, tranquilizing and anxiolytic activities. They influence, in particular, the central nervous system and are thus suitable as psychopharmaceuticals.

The compounds of this invention are particularly useful as agents to reverse the effects of benzodiazepines, especially in cases of overdosage. They are also useful as vigilance enhancers.

It is known that certain sites in the central nervous system of vertebrates show a high specific affinity for binding 1,4- and 1,5-benzodiazepines (Squires, R. F. and Braestrup, C., Nature (London) 266 (1977) 734). The sites are called benzodiazepine receptors. It has been found that the substituted β-carbolines of general Formula I, although greatly different in their chemical structure from benzodiazepines, surprisingly exhibit a strong affinity and specificity for binding to these benzodiazepine receptors in that they displace radioactively tagged flunitrazepam from these benzodiazepine receptors.

The displacement activity of the compounds of the invention is indicated in the table below as the IC$_{50}$ and ED$_{50}$ values. The IC$_{50}$ value indicates the concentration effecting a 50% displacement of the specific binding of $^3$H flunitrazepam (1.0 nM, 0° C.) in specimens with a total volume of 0.55 ml of a cerebral membrane suspension, for example from rats.

The displacement activity is determined by in vitro test as follows:

0.5 ml of a suspension of untreated rat cerebrum in 25 mM kH$_2$PO$_4$, pH=7.1 (5-10 mg of tissue/specimen) is incubated for 40-60 minutes at 0° C. together with $^3$H diazepam (specific activity 14.4 Ci/mmol, 1.9 nM) or $^3$H flunitrazepam (specific activity 87 Ci/mmol, 1.0 nM). After incubation, the suspension is filtered through a porous glass plate, the residue is washed twice with cold buffer solution, and the radioactivity is measured by means of a scintillation counter.

Then the test is repeated but in such a way that, prior to adding the radioactively tagged benzodiazepine, there is introduced a certain quantity or an excess amount of the compound, the displacement activity of which is to be determined. The IC$_{50}$ value is calculated on the basis of the thus-obtained data.

The ED$_{50}$ value represents the dose of a test compound effecting a reduction of the specific binding of flunitrazepam to the benzodiazepine receptor in a living brain to 50% of the control value.

The in vivo test is performed as follows:

Groups of mice are injected with the test compound at varying doses and normally subcutaneously. After 15 minutes, the mice receive the $^3$H flunitrazepam intravenously. After another 20 minutes, the mice are sacrificed, their forebrain membranes are removed, and the radioactivity of the forebrain membranes is measured by scintillation counter. The ED$_{50}$ value is determined with the aid of the dose/effect curves.

TABLE

Displacement Activity of Substituted β-Carboline Derivatives of Formula I

| Substitutent | | | IC$_{50}$ ng/ml (in vitro) | ED$_{50}$ mg/ml (in vivo) |
| --- | --- | --- | --- | --- |
| $R^3$ | $R^4$ | $R^{4**}$ | | |
| CO$_2$Me | H | H* | 1.9 | 22 |
| CO$_2$Et | CH$_3$ | CON(Allyl)$_2$ | 0.4 | 9.5 |
| CO$_2$Et | H | 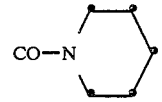 | 0.6 | 8.1 |
| CO$_2$Et | Me | COOC$_3$H$_7$ | 0.5 | 4.9 |
| CO$_2$Et | CH$_2$OCH$_3$ | CON(CH$_3$)$_2$ | 1.3 | 12 |
| 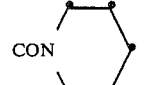 | H | 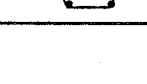 | 0.6 | 6.7 |

*Nature 294: 472 (1981)
**6-position

Based on their biological efficacy in the foregoing tests, in addition to their pharmacological uses, the compounds of this invention can be used as psychopharmaceuticals in human medicine. In this connection, they can be utilized formulated into pharmaceutical preparations, for example for oral and parenteral administration.

Formulating aids suitable herein are physiologically compatible, organic and inorganic excipients inert with respect to the compounds of this invention.

Examples for excipients are water, salt solutions, alcohols, polyethylene glycols, polyhydroxyethoxylated castor oil, gelatin, lactose, amylose, magnesium stearate, talc, silicic acid, fatty acid mono- and diglycerides, pentaerythritol fatty acid esters, hydroxymethylcellulose, and polyvinylpyrrolidone.

The pharmaceutical preparations can be sterilized and/or combined with auxiliary agents, such as lubricants, preservatives, stabilizers, wetting agents, emulsifiers, buffers, and colorants.

Especially suitable for parenteral administration are injection solutions or suspensions, particularly aqueous solutions of the active compounds in polyhydroxyethoxylated castor oil.

For oral administration, particularly suited are tablets, dragees, or capsules with talc and/or a hydrocarbon excipient or binder, e.g., lactose, cornstarch or potato starch. Use can also be in liquid form, for example as an elixir to which a sweetener is added, if desired.

The compounds of this invention are admixed in dosage units of 0.05–10 mg of active ingredient with a physiologically acceptable carrier or excipient.

The compounds of this invention are generally administered in a dosage of 0.1–300 mg/day, preferably 1–30 mg/day.

The compounds of this invention according to general Formula I are produced according to methods known per se.

To produce compounds of Formula I wherein $R^4$ is an $R^6$-oxycarbonyl group, the corresponding 6-halo-$\beta$-carboline derivative is carboxylated together with the corresponding alcohol of the formula $R^6OH$ in the presence of an alkaline catalyst, e.g., tributylamine, and a palladium(II) salt, e.g., palladium(II) acetate, under a carbon monoxide atmosphere at a temperature above room temperature in the range of 100° C.

For producing compounds of Formula I wherein $R^4$ or $R^3$ represents the grouping $CONR^{11}R^{12}$ and $CONR^7R^8$, respectively, the corresponding $\beta$-carboline-3- or $\beta$-carboline-6-carboxylic acid chloride is reacted in a suitable inert solvent, such as tetrahydrofuran, acetonitrile, methylene chloride, chloroform, or dioxane, suitably under cooling, with a primary or secondary amine of the formula $NHR^{11}R^{12}$ and $NHR^7R^8$, respectively.

In order to obtain compounds of Formula I wherein $R^3$ is a 5-oxadiazolyl group, the corresponding free $\beta$-carboline-3-carboxylic acid is condensed with an amidoxime of the formula $R^5-C(=NOH)NH_2$ wherein $R^5$ is a lower alkyl, in a solvent boiling above 100° C. and inert with respect to the reactants, at the reflux temperature of the reaction mixture. Suitable solvents for the condensation reaction are, for example, toluene and dimethylformamide. Suitably, the free $\beta$-carboline-3-carboxylic acid is activated in a suitable way prior to the condensation reaction. For this purpose, the free acid can be converted into the mixed anhydride, the activated ester, or the chloride. Activation with imidazole/thionyl chloride in an aprotic solvent, such as dioxane, tetrahydrofuran, dimethylformamide, or N-methylpyrrolidone at temperatures of between 0° and 50° C., preferably room temperature, proved advantageous.

For the production of compounds of Formula I wherein $R^3$ is a piperidino-oxycarbonyl group, the free $\beta$-carboline-3-carboxylic acid is reacted in an inert solvent in succession with ethyl chloroformate in the presence of an alkaline catalyst, such as, for example, triethylamine, at temperatures below room temperature, preferably below 0° C., and finally with piperidine.

In order to produce a free $\beta$-carboline-6-carboxylic acid, an aralkyl group, such as the benzyl group, can be removed by hydrogenation, as in the $\beta$-carboline-6-carboxylic acid benzyl ester. For this purpose, the 6-benzyl ester is hydrogenated on palladium in methanolic hydrochloric acid. With this method, a 3-alkoxycarbonyl group that may be present on the $\beta$-carboline molecule is not affected.

For production of a free $\beta$-carboline-3-carboxylic acid, the corresponding ester is hydrolyzed in an aliphatic alcohol, such as methanol or ethanol with a dilute aqueous alkali, such as sodium or potassium hydroxide solution, at the boiling temperature of the reaction mixture.

For esterification of a free $\beta$-carboline-3-carboxylic acid, the latter is converted into the cesium salt with cesium carbonate and subsequently made to react with the corresponding alkyl halogenide.

For transesterification, the corresponding ester of Formula I is heated in the presence of catalytic amounts of the corresponding sodium alcoholate or sodium hydride with the desired alcohol for 3–6 hours to temperatures of between 60° and 120° C. Optionally, transesterification can also be effected with this alcohol in the presence of an acidic catalyst, such as p-toluenesulfonic acid, hydrochloric acid, or copper(II) chloride.

For preparing compounds of Formula I wherein the substituent $R^4$ means $CSNR^{11}R^{12}$, the corresponding carbonyl compound is treated in a suitable solvent with a polysulfide, such as phosphorus pentasulfide or Lawesson's reagent in the presence of a base. Suitable solvents are, for example, tetrahydrofuran, toluene, acetonitrile, and glycol dimethyl ether. Examples of suitable bases are sodium bicarbonate and potassium carbonate.

The starting $\beta$-carbolines of Formulae II, III and IV also can be produced by conventional methods, e.g., U.S. Pat. No. 4,371,536 and U.S. Pat. No. 4,435,403.

Contemplated equivalents of the compounds of general Formula I are compounds otherwise corresponding thereto and having the same general properties wherein one or more of $R^4$ and $R^5$ to $R^{12}$ are simple variations of the substituents as defined therein, e.g., wherein any of $R^4$ to $R^{12}$, can be a high or substituted alkyl group. As will be apparent, where a substituent can be a hydrogen atom, the exact chemical nature of a substituent which is other than hydrogen at that position is not critical, so long as it does not adversely affect the overall spectrum of activity of the $\beta$-carboline.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

PREPARATION OF STARTING MATERIAL (A) 6-Iodo-4-methyl-$\beta$-carboline-3-carboxylic Acid Ethyl Ester 5.08 g of 4-methyl-$\beta$-carboline-3-carboxylic acid ethyl ester is dissolved in 40 ml of glacial acetic acid and combined with 0.96 ml of water, 0.24 ml of concentrated sulfuric acid, 688 mg of iodic acid, and 1.768 mg of iodine. The mixture is heated to 80° C. for 3 hours. After cooling, the mixture is suctioned off from undissolved material, and the filtrate is evaporated. The residue is taken up in ethanol/water. The thus-formed crystals are suctioned off, taken up in 500 ml of ethyl acetate, and extracted by stirring with 200 ml of 1N sodium hydroxide solution for 15 minutes. The organic phase is separated, concentrated by evaporation, the residue is extracted by stirring in ethyl acetate, and vacuum-filtered, thus obtaining 4.3 g of 6-iodo-4-methyl-$\beta$-carboline-3-carboxylic acid ethyl ester, mp 250°–255° C.

The 4-ethyl-6-iodo-β-carboline-3-carboxylic acid ethyl ester is produced analogously.

(B) 3-Ethoxycarbonyl-4-ethyl-β-carboline-6-carboxylic Acid Chloride and Homologs 590 mg of 3-ethoxycarbonyl-4-ethyl-β-carboline-6-carboxylic acid is refluxed in 6 ml of thionyl chloride with a drop of dimethylformamide for 2.5 hours. After evaporation and drying, 664 mg of 3-ethoxycarbonyl-4-ethyl-β-carboline-6-carboxylic acid chloride is obtained in the form of the hydrochloride.

The following compounds are furthermore produced:
3-ethoxycarbonyl-4-methyl-β-carboline-6-carboxylic acid chloride,
3-ethoxycarbonyl-4-methoxymethyl-β-carboline-6-carboxylic acid chloride, and
3-ethoxycarbonyl-β-carboline-6-carboxylic acid chloride.

EXAMPLE 1

1.97 g of 6-iodo-4-ethyl-β-carboline-3-carboxylic acid ethyl ester is heated under a carbon monoxide atmosphere in 30 ml of benzyl alcohol together with 1.34 ml of tributylamine to 100° C. Then 55 mg of palladium(II) acetate is added thereto, the mixture is well flushed with carbon monooxide, and stirred at 100° C. for 2 hours. After the benzyl alcohol has been removed by distillation, the residue is taken up in 300 ml of methylene chloride, washed in succession with 80 ml of 1N hydrochloric acid, 100 ml of semisaturated sodium bicarbonte solution, as well as 100 ml of saturated sodium chloride solution, dried, filtered, and concentrated. Recrystallization from ethanol/petroleum ether yields 980 mg of 6-benzyloxycarbonyl-4-ethyl-β-carboline-3-carboxylic acid ethyl ester, mp 212°–215° C.

The following compounds are produced analogously:
6-butoxycarbonyl-4-methyl-β-carboline-3-carboxylic acid ethyl ester, mp 179°–186° C.;
6-propoxycarbonyl-4-methyl-β-carboline-3-carboxylic acid ethyl ester, mp 235°–240° C. (ethanol);
6-benzyloxycarbonyl-4-methyl-β-carboline-3-carboxylic acid ethyl ester;
6-benzyloxycarbonyl-4-methoxymethyl-β-carboline-3-carboxylic acid ethyl ester, mp 183°–185° C. (ethyl acetate/hexane);
6-benzyloxycarbonyl-β-carboline-3-carboxylic acid ethyl ester, mp 265°–272° C. (dimethylformamide);
6-(2-methoxyethyl)oxycarbonyl-β-carboline-3-carboxylic acid ethyl ester, mp 169°–174° C. (ethanol/hexane);
6-butoxycarbonyl-4-methyl-β-carboline-3-carboxylic acid butyl ester, mp 140°–145° C.;
6-butoxycarbonyl-4-methoxymethyl-β-carboline-3-carboxylic acid ethyl ester, mp 150°–152° C. (ethanol/hexane); and
3-(5'-[3'-ethyl-1',2',4'-oxadoazol]yl)-β-carboline-6-carboxylic acid ethyl ester, mp >330° C. (decomposition).

EXAMPLE 2

At room temperature and under normal pressure, 970 mg of 6-benzyloxycarbonyl-4-ethyl-β-carboline-3-carboxylic acid ethyl ester is hydrogenated for one hour in 50 ml of methanol with 3 ml of 1N hydrochloric acid and 1.50 g of 10% palladium/carbon. After the catalyst has been removed by filtration, the mixture is evaporated, thus obtaining 593 mg of 3-ethoxycarbonyl-4-ethyl-β-carboline-6-carboxylic acid as the hydrochloride.

The following compounds are produced as the hydrochlorides in analogous fashion:
3-ethoxycarbonyl-4-methyl-β-carboline-6-carboxylic acid, mp 328°–330° C. (ethanol);
3-ethoxycarbonyl-4-methoxymethyl-β-carboline-6-carboxylic acid;
3-ethoxycarbonyl-β-carboline-6-carboxylic acid, mp 313°–314° C. (decomposition; ethanol/ethyl acetate); and
3-ethoxycarbonyl-β-carboline-5-carboxylic acid.

EXAMPLE 3

Under ice cooling, dimethylamine is introduced for 10 minutes into a suspension of 322 mg of 3-ethoxycarbonyl-4-ethyl-β-carboline-6-carboxylic acid chloride (as the hydrochloride) in 10 ml of tetrahydrofuran. The mixture is then allowed to warm up to room temperature and stirred for another hour at room temperature. After evaporation, the mixture is distributed in ethyl acetate/saturated sodium bicarbonate solution, and the organic phase is washed with 25 ml of saturated sodium chloride solution, dried, filtered, and concentrated. Recrystallization from ethanol/hexane yields 175 mg of 6-N,N-dimethylcarbamoyl-4-ethyl-β-carboline-3-carboxylic acid ethyl ester, mp 169°–170° C.

Analogously, the following compounds are prepared:
6-N,N-dimethylcarbamoyl-4-methyl-β-carboline-3-carboxylic acid ethyl ester, mp 224°–225° C. (ethanol/hexane);
6-N,N-dimethylcarbamoyl-4-methoxymethyl-β-carboline-3-carboxylic acid ethyl ester, mp 131°–133° C. (ethyl acetate/diisopropyl ether); and
6-N,N-dimethylcarbamoyl-β-carboline-3-carboxylic acid ethyl ester, mp 185°–196° C.

EXAMPLE 4

Under ice cooling, 0.21 ml of diallylamine is added to a suspension of 372 mg of 3-ethoxycarbonyl-4-ethyl-β-carboline-6-carboxylic acid chloride (hydrochloride) in 10 ml of tetrahydrofuran. After 2 hours of agitation, the mixture is evaporated, distributed in ethyl acetate/saturated sodium bicarbonate solution, the organic phase is dried, filtered, and concentrated. After chromatography over silica gel with methylene chloride/ethanol=10:1 as the eluent, 266 mg of 6-N,N-diallylcarbamoyl-4-ethyl-β-carboline-3-carboxylic acid ethyl ester is obtained as an oil.

The following compounds are produced analogously:
6-N,N-diethylcarbamoyl-4-methyl-β-carboline-3-carboxylic acid ethyl ester, mp 218°–220° C. (ethanol/hexane);
6-morpholinocarbonyl-4-methyl-β-carboline-3-carboxylic acid ethyl ester, mp 199°–201° C. (ethanol, diethyl ether/hexane);
6-N,N-diallylcarbamoyl-4-methyl-β-carboline-3-carboxylic acid ethyl ester (oil);
6-pyrrolidinocarbonyl-4-methyl-β-carboline-3-carboxylic acid ethyl ester, mp 272°–274° C. (ethanol/hexane);
6-(4-phenylpiperazino)carbonyl-4-methyl-β-carboline-3-carboxylic acid ethyl ester, mp 226°–228° C. (ethanol/hexane);
6-(4-methylpiperazino)carbonyl-4-methyl-β-carboline-3-carboxylic acid ethyl ester, mp 228°–229° C. (ethanol/hexane);

6-(thiomorpholino)carbonyl-4-methyl-β-carboline-3-carboxylic acid ethyl ester, mp 180°–182° C. (ethanol/hexane);

6-diallylcarbamoyl-4-methoxymethyl-β-carboline-3-carboxylic acid ethyl ester;

6-diallylcarbamoyl-β-carboline-3-carboxylic acid ethyl ester, mp 189°–191° C. (cyclohexane/ethyl acetate);

6-piperidinocarbonyl-β-carboline-3-carboxylic acid ethyl ester, mp 237°–240° C.; and 6-piperidinocarbonyl-β-carboline-3-carboxylic acid piperidide, mp 267°–269° C.

EXAMPLE 5

A suspension of 320 mg of 3-ethoxycarbonyl-β-carboline-6-carboxylic acid chloride (hydrochloride) in 10 ml of tetrahydrofuran and 8 ml of methylene chloride is combined with 83.5 mg of methylammonium hydrochloride and 0.6 ml of triethylamine. After standing overnight at room temperature, the mixture is combined with water and glacial acetic acid, extensively evaporated, and distributed in ethyl acetate/saturated sodium bicarbonate solution. The organic phase is dried, concentrated, and the residue chromatographed over silica gel with methylene chloride/ethanol=10:1. After recrystallization of the corresponding fractions from ethanol/hexane, 25 mg of 6-N-methylcarbamoyl-4-methyl-β-carboline-3-carboxylic acid ethyl ester is obtained, mp 224°–225° C.

EXAMPLE 6

700 mg of 6-iodo-4-methyl-β-carboline-3-carboxylic acid ethyl ester is combined in 18 ml of piperidine with 0.6 ml of tributylamine and heated under a carbon monoxide atmosphere to 60° C. At this temperature, 18 mg of bis[tri(o-tolyl)phosphine]palladium(II) dichloride is added, the mixture is purged well with carbon monoxide, and then the batch is heated for 2.5 hours to 80° C. After dilution with methylene chloride, the mixture is filtered and evaporated. The residue is distributed in methylene chloride and 1N hydrochloric acid, the organic phase is washed twice with 1N hydrochloric acid, with dilute ammonia, with water, dried, filtered, and concentrated. Recrystallization from ethyl acetate yields 400 mg of 6-piperidinocarbonyl-4-methyl-β-carboline-3-carboxylic acid ethyl ester, mp 212°–218° C.

EXAMPLE 7

400 mg of 6-piperidinocarbonyl-4-methyl-β-carboline-3-carboxylic acid ethyl ester is heated in 16 ml of toluene with 200 mg of Lawesson's reagent [2,4-bis(4-methoxyphenyl)-1,3-dithiaphosphetane-2,4-disulfide] for one hour to 100° C. Thereafter the mixture is combined with water and extracted twice with ethyl acetate. The ethyl acetate phase is dried, filtered, concentrated, and chromatographed over silica gel with methylene chloride/ethanol=10:1. Recrystallization of the corresponding fractions from ethanol/water yields 240 mg of 6-piperidinothiocarbonyl-4-methyl-β-carboline-3-carboxylic acid ethyl ester, mp 225°–230° C.

EXAMPLE 8

202 mg of 3-ethoxycarbonyl-4-methoxymethyl-β-carboline-6-carboxylic acid is combined in 15 ml of ethanol and 5 ml of water with 206 mg of cesium carbonate in 1.5 ml of water and stirred until a clear solution is obtained. The solution is then evaporated to dryness, taken up in 10 ml of dimethylformamide, 0.14 ml of methyl iodide is added, and the mixture is agitated at room temperature for 3 hours. After evaporation, the mixture is distributed in methylene chloride/saturated sodium chloride solution. The organic phase is dried, filtered, concentrated, and chromatographed over silica gel with methylene chloride/ethanol=6:1 as the eluent. After recrystallization of the corresponding fractions from ethanol/hexane, 92 mg of 6-methoxycarbonyl-4-methoxymethyl-β-carboline-3-carboxylic acid ethyl ester is obtained.

The following compounds are analogously produced:

6-isopropoxycarbonyl-4-methyl-β-carboline-3-carboxylic acid ethyl ester, mp 190°–191° C. (ethanol/hexane); and 6-ethoxycarbonyl-4-methoxymethyl-β-carboline-3-carboxylic acid ethyl ester, mp 193° C.

EXAMPLE 9

Under agitation and cooling, dimethylamine is introduced for 10 minutes into a suspension of 300 mg of 3-ethoxycarbonyl-β-carboline-6-carboxylic acid chloride (hydrochloride) in 10 ml of tetrahydrofuran. The mixture is then stirred for 17 hours at room temperature. After concentration, the residue is distributed in ethyl acetate/saturated sodium bicarbonate solution. The organic phase is dried, filtered, concentrated, and chromatographed over silica gel with methylene chloride/methanol=10:2 as the eluent. Yield: 43 mg of 3,6-bis(N,N-dimethylcarbamoyl)-β-carboline.

EXAMPLE 10

345 mg of 6-N,N-dimethylcarbamoyl-β-carboline-3-carboxylic acid ethyl ester is refluxed for ½ hour in 10 ml of ethanol with 2 ml of 1N aqueous potassium hydroxide solution. After cooling, 0.45 ml of glacial acetic acid is added dropwise, and the mixture is diluted with a small amount of water. After vacuum filtering and washing with ethanol and water, 283 mg of 6-N,N-dimethylcarbamoyl-β-carboline-3-carboxylic acid is obtained, mp 295°–297° C. (decomposition).

The following compounds are analogously prepared:

6-N,N-dimethylcarbamoyl-4-methyl-β-carboline-3-carboxylic acid, mp 272° C.;

6-piperidinocarbonyl-4-methyl-β-carboline-3-carboxylic acid, mp 291° C. (decomposition); and 6-piperidinocarbonyl-β-carboline-3-carboxylic acid, mp 271°–275° C. (decomposition).

EXAMPLE 11

A mixture of 0.5 g of thionyl chloride in 10 ml of absolute tetrahydrofuran is added dropwise under agitation to a solution of 1.35 g of imidazole in 25 ml of tetrahydrofuran. After 15 minutes of agitation, the mixture is filtered and 0.8 g of 4-methyl-6-N,N-dimethylcarbamoyl-β-carboline-3-carboxylic acid is added to the filtrate. After 18 hours of agitation, the thus-produced suspension is combined with 1.25 g of propionamidoxime and stirred for one hour at room temperature. After standing overnight, the mixture is concentrated by evaporation, taken up in 30 ml of toluene, and refluxed for 3 hours. After evaporation, distribution in methylene chloride/water, drying, filtration of the organic phase, and evaporation of the organic phase, as well as recrystallization, 300 mg of 4-methyl-3-(5'-[3'-ethyl-1',2',4'-oxadiazol]yl)-β-carboline-6-carboxylic acid dimethylamide is obtained, mp 268°–272° C.

Analogously, the 3-(5'-[3'-ethyl-1',2',4'-oxadiazol]yl)-β-carboline-6-carboxylic acid ethyl ester, mp >330° C.

(decomposition) is obtained from the β-carboline-3-carboxylic acid-6-carboxylic acid ethyl ester.

Furthermore, the following compounds are analogously produced:

3-(5′-[3′-ethyl-1′,2′,4′-oxadiazol]yl)-β-carboline-6-carboxylic acid N,N-dimethylamide;

3-(5′-[3′-ethyl-1′,2′,4′-oxadiazol]yl)-β-carboline-6-carboxylic acid piperidide, mp 291°–295° C.; and 3-(5′-[3′-ethyl-1′,2′,4′-oxadiazol]yl)-4-methyl-β-carboline-6-carboxylic acid piperidide, mp 243°–245° C.

EXAMPLE 12

A solution is prepared from 280 mg of 6-N,N-dimethylcarbamoyl-4-methyl-β-carboline-3-carboxylic acid and 15 ml of dimethylformamide. After cooling the solution to −5° C., 0.14 ml of triethylamine is first added dropwise and then 0.096 ml of ethyl chloroformate is added dropwise thereto. The mixture is stirred at this temperature for 5 minutes and then 0.1 ml of piperidine is added in 1 ml of dimethylformamide. After agitation overnight at room temperature, the mixture is concentrated by evaporation, the residue is distributed in methylene chloride/dilute ammonia solution, the organic phase is dried, filtered, and concentrated. Chromatography of the residue over silica gel with methylene chloride/ethanol=10:1 yields 50 mg of 6-N,N-dimethylcarbamoyl-4-methyl-β-carboline-3-carboxylic acid piperidide.

6-Piperidinocarbonyl-β-carboline-3-carboxylic acid piperidide, mp 267°–269° C., is prepared analogously.

EXAMPLE 13

Under a carbon monoxide atmosphere, 320 mg of 5-bromo-β-carboline-3-carboxylic acid ethyl ester is heated in 6 ml of benzyl alcohol with 0.27 ml of tributylamine to 110° C. Then 76 mg of palladium bis(tri-o-tolylphosphine)dichloride is added, and the mixture is heated under carbon monoxide for 4 hours. Thereafter another 38 mg of catalyst is added and the mixture is heated for one hour to 110° C. under carbon monoxide. After evaporation to dryness, the mixture is taken up in dimethylformamide and filtered off from the catalyst. After evaporation, the residue is chromatographed over silica gel with chloroform/methanol=10:1.5 as the eluent. Crystallization from ethyl acetate/diisopropyl ether yields 94 mg of 5-benzyloxycarbonyl-β-carboline-3-carboxylic acid ethyl ester, mp 150°–155° C.

EXAMPLE 14

Analogously to Example 4, the 5-piperidinocarbonyl-β-carboline-3-carboxylic acid ethyl ester is obtained as an oily compound from 3-ethoxycarbonyl-β-carboline-5-carboxylic acid via the intermediate stage of the acid chloride (see preparation of the starting material in Example B).

What is claimed is:

1. A β-carboline of the formula

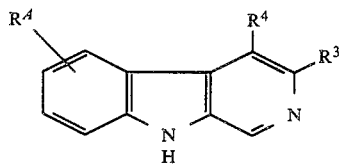

wherein
R$^3$ is an oxadiazolyl group of the formula

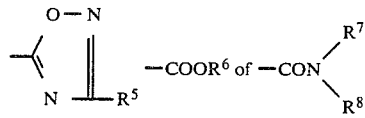

wherein R$^5$ is lower alkyl of up to 5 carbon atoms, R$^6$ is lower alkyl, aralkyl, or alkoxyalkyl of up to 7 carbon atoms, and R$^7$ and R$^8$ which are alike or different, each are hydrogen or lower alkyl of up to 5 carbon atoms or collectively form with the amido nitrogen atom a piperidino ring;

R$^4$ is hydrogen, lower alkyl of up to 3 carbon atoms or CH$_2$OR$^9$ wherein R$^9$ is lower alkyl of up to 3 carbon atoms; and R$^4$ is in the 5- or 6-position and is —COOR$^{10}$ or

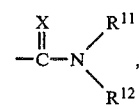

wherein R$^{10}$ is alkoxyalkyl or alkenyl of up to 5 carbon atoms, or benzyl, wherein X is oxygen or sulfur and R$^{11}$ and R$^{12}$, which are alike or different, are hydrogen, lower alkyl or lower alkenyl or, collectively with the amido nitrogen atom, form morpholino, thiomorpholino, pyrrolidino, piperazino, 4-phenyl-piperazino, 4-methylpiperazino or piperidino.

2. A β-carboline of claim 1, wherein R$^4$ is in the 6-position.

3. A β-carboline of claim 2, wherein R$^3$ is —COOR$^6$ and R$^4$ is —COOR$^{10}$ in which R$^6$, and R$^{10}$ have the values given therein.

4. A β-carboline of claim 2, wherein R$^3$ is —COOR$^6$ and R$^4$ is —CONR$^{11}$R$^{12}$ in which R$^6$, R$^{11}$ and R$^{12}$ have the values given therein.

5. A compound of claim 2, wherein R$^3$ is an oxadiazolyl group as defined therein.

6. A pharmaceutical composition comprising an amount of compound of claim 1 effective to reverse the effects of a benzodiazepine, in admixture with a pharmaceutically acceptable carrier.

7. 6-benzyloxycarbonyl-4-ethyl-β-carboline-3-carboxylic acid ethyl ester, a compound of claim 1.

8. 6-benzyloxycarbonyl-4-methyl-β-carboline-3-carboxylic acid ethyl ester, a compound of claim 1.

9. 6-benzyloxycarbonyl-4-methoxymethyl-β-carboline-3-carboxylic acid ethyl ester, a compound of claim 1.

10. 6-benzyloxycarbonyl-β-carboline-3-carboxylic acid ethyl ester, a compound of claim 1.

11. 6-(2-methoxyethyl)oxycarbonyl-β-carboline-3-carboxylic acid ethyl ester, a compound of claim 1.

12. 6-N,N-dimethylcarbamoyl-4-ethyl-β-carboline-3-carboxylic acid ethyl ester, a compound of claim 1.

13. 6-N,N-dimethylcarbamoyl-4-methyl-β-carboline-3-carboxylic acid ethyl ester, a compound of claim 1.

14. 6-N,N-dimethylcarbamoyl-4-methoxymethyl-β-carboline-3-carboxylic acid ethyl ester, a compound of claim 1.

15. 6-N,N-dimethylcarbamoyl-β-carboline-3-carboxylic acid ethyl ester, a compound of claim 1.

16. 6-N,N-diallylcarbamoyl-4-ethyl-β-carboline-3-carboxylic acid ethyl ester, a compound of claim 1.

17. 6-N,N-diethylcarbamoyl-4-methyl-β-carboline-3-carboxylic acid ethyl ester.

18. 6-morpholinocarbonyl-4-methyl-β-carboline-3-carboxylic acid ethyl ester, a compound of claim 1.

19. 6-N,N-diallylcarbamoyl-4-methyl-β-carboline-3-carboxylic acid ethyl ester, a compound of claim 1.

20. 6-pyrrolidinocarbonyl-4-methyl-β-carboline-3-carboxylic acid ethyl ester, a compound of claim 1.

21. 6-(4-phenylpiperazino)carbonyl-4-methyl-β-carboline-3-carboxylic acid ethyl ester, a compound of claim 1.

22. 6-(4-methylpiperazino)carbonyl-4-methyl-β-carboline-3-carboxylic acid ethyl ester, a compound of claim 1.

23. 6-(thiomorpholino)carbonyl-4-methyl-β-carboline-3-carboxylic acid ethyl ester, a compound of claim 1.

24. 6-diallylcarbamoyl-4-methoxymethyl-β-carboline-3-carboxylic acid ethyl ester, a compound of claim 1.

25. 6-diallylcarbamoyl-β-carboline-3-carboxylic acid ethyl ester, a compound of claim 1.

26. 6-piperidinocarbonyl-β-carboline-3-carboxylic acid ethyl ester, a compound of claim 1.

27. 6-piperidinocarbonyl-β-carboline-3-carboxylic acid piperidide, a compound of claim 1.

28. 6-N-methylcarbamoyl-4-methyl-β-carboline-3-carboxylic acid ethyl ester, a compound of claim 1.

29. 6-piperidinocarbonyl-4-methyl-β-carboline-3-carboxylic acid ethyl ester, a compound of claim 1.

30. 6-piperidino-thiocarbonyl-4-methyl-β-carboline-3-carboxylic acid ethyl ester, a compound of claim 1.

31. 3,6-bis(N,N-dimethylcarbamoyl)-β-carboline, a compound of claim 1.

32. 6-N,N-dimethylcarbamoyl-β-carboline-3-carboxylic acid, a compound of claim 1.

33. 6-N,N-dimethylcarbamoyl-4-methyl-β-carboline-3-carboxylic acid, a compound of claim 1.

34. 6-piperidinocarbonyl-4-methyl-β-carboline-3-carboxylic acid, a compound of claim 1.

35. 6-piperidinocarbonyl-β-carboline-3-carboxylic acid, a compound of claim 1.

36. 4-methyl-3-(5'-[3'-ethyl-1',2',4'-oxadiazol]yl)-β-carboline-6-carboxylic acid dimethylamide, a compound of claim 1.

37. 3-(5'-[3'-ethyl-1',2',4'-oxadiazol]yl)-β-carboline-6-carboxylic acid N,N-dimethylamide, a compound of claim 1.

38. 3-(5'-[3'-ethyl-1',2',4'-oxadiazol]yl)-β-carboline-6-carboxylic acid piperidide, a compound of claim 1.

39. 3-(5'-[3'-ethyl-1',2',4'-oxadiazol]yl)-4-methyl-β-carboline-6-carboxylic acid piperidide, a compound of claim 1.

40. 6-N,N-dimethylcarbamoyl-4-methyl-β-carboline-3-carboxylic acid piperidide, a compound of claim 1.

41. 6-piperidinocarbonyl-β-carboline-3-carboxylic acid piperidide, a compound of claim 1.

42. 5-benzyloxycarbonyl-β-carboline-3-carboxylic acid ethyl ester, a compound of claim 1.

43. 5-piperidinocarbonyl-β-carboline-3-carboxylic acid ethyl ester, a compound of claim 1.

44. A composition of claim 6 wherein the amount of said compound is 0.05–10 mg per unit dosage.

* * * * *

UNITED STATES PATENT AND TRADEMARK OFFICE
CERTIFICATE OF CORRECTION

PATENT NO. : 4,600,715
DATED : July 15, 1986
INVENTOR(S) : Andreas Huth et al

It is certified that error appears in the above-identified patent and that said Letters Patent is hereby corrected as shown below:

Column 12, lines 1-7: Formula should read as shown below

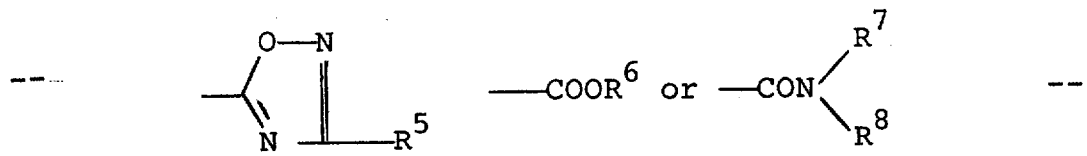

Signed and Sealed this

Seventh Day of October, 1986

[SEAL]

Attest:

DONALD J. QUIGG

Attesting Officer

Commissioner of Patents and Trademarks